United States Patent [19]

Stevens

[11] Patent Number: 5,514,108

[45] Date of Patent: May 7, 1996

[54] SOFT FLEXIBLE CATHETER TIP FOR USE IN ANGIOGRAPHY

[75] Inventor: Robert C. Stevens, Williston, Fla.

[73] Assignee: Cordis Corporation, Miami Lakes, Fla.

[21] Appl. No.: 299,841

[22] Filed: Sep. 1, 1994

[51] Int. Cl.⁶ .................................................. A61M 25/00
[52] U.S. Cl. ........................................ 604/280; 604/264
[58] Field of Search .................................. 604/280–282, 604/96, 19–27, 264

[56] References Cited

U.S. PATENT DOCUMENTS

| | | |
|---|---|---|
| D. 263,873 | 4/1982 | Genese . |
| 1,477,695 | 4/1920 | Dolge et al. . |
| 3,485,234 | 4/1966 | Stevens . |
| 4,576,772 | 3/1986 | Carpenter . |
| 4,596,563 | 6/1986 | Pande . |
| 4,661,094 | 4/1987 | Simpson . |
| 4,731,054 | 3/1988 | Billeter et al. . |
| 4,838,879 | 6/1989 | Tanabe et al. . |
| 5,017,259 | 5/1991 | Kohsai . |
| 5,088,991 | 2/1992 | Weldon . |

Primary Examiner—C. Fred Rosenbaum
Assistant Examiner—Perry E. VanOver
Attorney, Agent, or Firm—Fay, Sharpe, Beall, Fagan, Minnich & McKee

[57] ABSTRACT

A plurality of regions of a first transverse rigidity are formed in the flexible tip portion of a catheter having a second transverse rigidity along its length which is greater than the first transverse rigidity. The regions of the lesser first transverse rigidity are formed by areas of the catheter tip having an average transverse cross-sectional area less than a transverse cross-sectional area of the remainder of the catheter apparatus. The plurality of first transverse rigidity regions are formed by a respective plurality of circumferential cut out regions in the catheter tip.

18 Claims, 1 Drawing Sheet

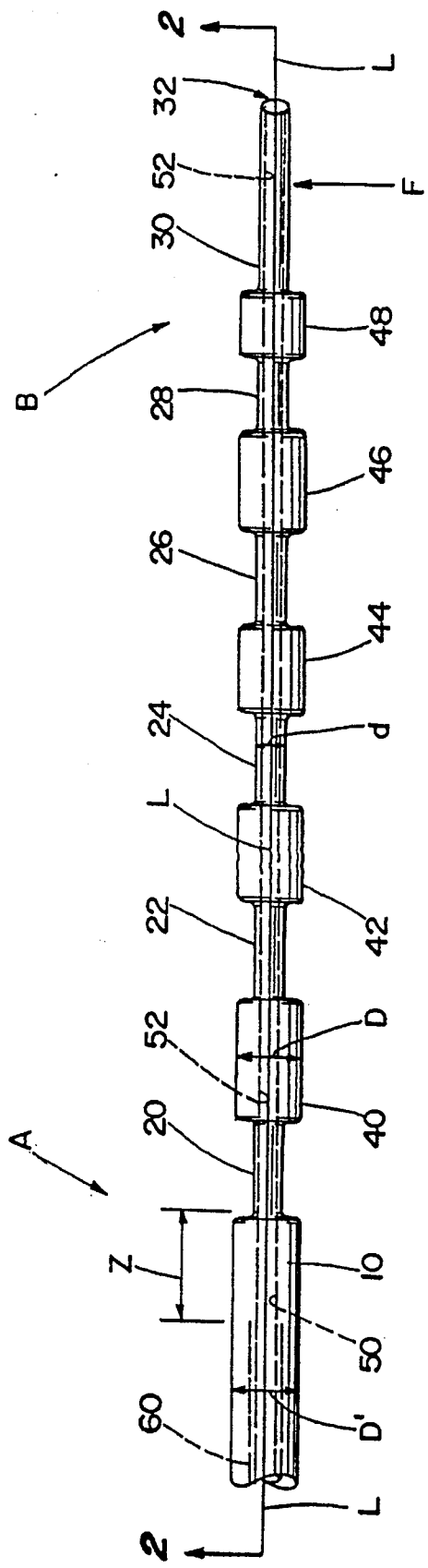
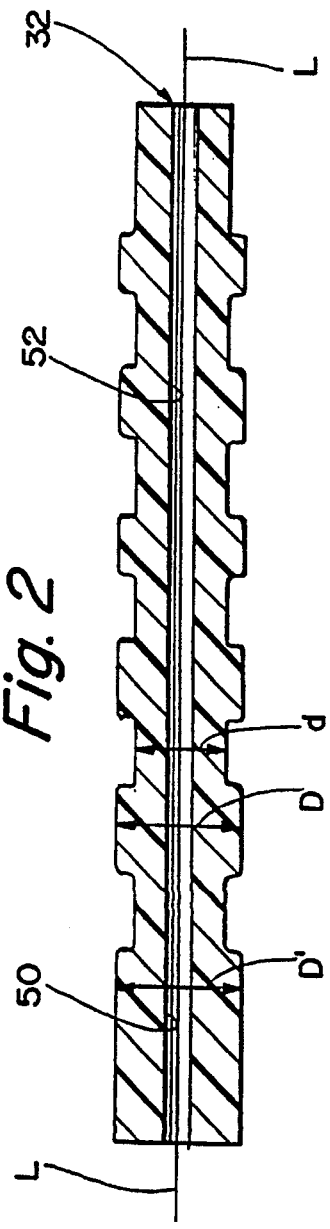
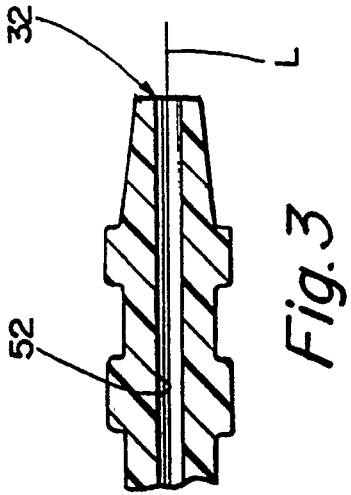

SOFT FLEXIBLE CATHETER TIP FOR USE IN ANGIOGRAPHY

BACKGROUND OF THE INVENTION

The instant invention relates to a catheter apparatus having a soft flexible tip adapted for use with a steel guide wire in procedures including angiography and will be described with particular reference thereto. However, it is to be appreciated that the invention finds application in other procedures where catheters are inserted generally into the human body cavity.

In the practice of catheterization and in particular angiography, a hollow catheter is inserted by well known means into the vascular system of a patient, usually through the femoral artery, and advanced toward a target site where an opaque media is delivered under pressure. During the procedure, it is important to accurately route the catheter through the appropriate branching vessels within the body. For this purpose, a small bend is oftentimes placed on or formed by the catheter tip so that rotational motion about the longitudinal axis of the catheter while advancing same effects a "steering" of the tip through the system.

In order to prevent damage to the patient yet provide a workable apparatus, the catheter tip must be both soft so as to be incapable of distending or piercing the surrounding vessels yet transversely rigid enough to withstand both the motion of blood flow as well as stand-up under the opaque media delivery pressure.

A catheter tip that is too soft tends to curl upon itself and become lodged in the tissue and vessel wall. Further, a tip which is too soft to be forced into and through the vessel at the artery site, such as into the femoral artery, is of little utility at all. Catheter tips which are to rigid are difficult to control as they are routed to the target site. Damage to the vessels and arteries or other body tissue may result from the use of stiff catheter tips.

SUMMARY OF THE INVENTION

The present invention contemplates a new and improved flexible catheter tip apparatus adapted to be guided through blood vessels. The catheter tip of the invention includes at least one region of a transverse rigidity disposed in the flexible catheter tip being different from the average overall transverse rigidity of the remainder of the catheter device. The catheter apparatus includes an elongate tubular member having a substantially uniform first transverse rigidity while the flexible tip portion of the catheter device includes a series of portions of varying transverse rigidity to provide a region of a second average transverse rigidity less than the first transverse rigidity.

According to another aspect of the invention, the second average transverse rigidity of the at least one region of the flexible catheter tip varies along the longitudinal axis of the flexible tip portion.

According to a further aspect of the invention, the at least one region of varying second transverse rigidity is defined by a portion of the flexible tip having an average transverse first cross-sectional area along the longitudinal axis of the catheter which is less than a transverse second cross-sectional area of the remainder of the catheter flexible tip.

According to still another aspect of the invention, at least one region of varying second average transverse rigidity includes a plurality of portions, each of the plurality of regions having a respective transverse rigidity less than the first transverse rigidity. More particularly, the regions of lesser transverse rigidity can be provided by areas of lesser wall thickness as, for example, results from a construction which is in the nature of a series of rings of differing outer diameter but of common inner diameter.

According to yet another aspect of the invention, the catheter includes a single, uniform longitudinal bore formed therethrough which serves as a conduit for the transport of opaque media during surgical procedures.

An advantage of the invention is that it provides an improved surgical risk quotient whereby the chances of injury to the patient are minimized.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, the preferred embodiment of which will be described in detail in this specification and illustrated in the accompanying drawings which form a part hereof, and wherein:

FIG. 1 is a side view of the distal end region of an angiographic catheter in accordance with the present invention;

FIG. 2 is a longitudinal cross-sectional view of the angiographic catheter of FIG. 1 taken along line 2—2; and FIG. 3 is a longitudinal cross-section showing a modified distal end for the angiographic catheter of FIG. 1.

DETAILED DESCRIPTION OF THE PREFERRED EMBODIMENTS

Referring now to the drawings wherein the showings are for the purposes of illustrating the preferred embodiment of the invention only and not for the purposes of limiting same, the figures show (not to scale) a catheter device A having a distal end B adapted to be guided through blood vessels of a human patient. More particularly, and with reference first to FIG. 1, the catheter device A forms an elongate tubular body member 10 which connects the proximal end (not shown) of the catheter device with the distal end B for conducting opaque media from an operatively associated source of the media to the distal end B. A flexible tip portion 12 is formed at the distal end B of the catheter device A.

According to the preferred embodiment, the flexible tip portion includes a plurality of regions having a transverse rigidity different than the transverse rigidity inherent in the construction of the elongate tubular body member 10. For the purposes of this detailed description, "transverse rigidity" defines that property of an elongate body which tends to resist bending in a direction substantially perpendicular to the longitudinal axis of that elongate body. With reference to FIG. 1, the transverse rigidity of the catheter device shown there is its ability to resist bending due to forces such as shown at F which are generally applied perpendicular and generally transverse to the longitudinal axis L of the catheter. The transverse rigidity of the present invention varies from the distal end longitudinally to the proximal end and the average transverse rigidity of the tip portion 12 decreases from body 10 to the distal end and is less than the transverse rigidity of body 10.

With continued reference to FIG. 1, in the preferred embodiment, the varying regions of transverse rigidity formed in the flexible tip portion 12 are generated by a plurality of cut out regions 20–30 which may either be formed in the flexible tip portion during its manufacture or defined thereon in one or more additional manufacturing step(s) such as a cutting or roll forming operation.

The plurality of cut out regions 20–30 define a plurality of spaced apart circumferential rings 40–48 arranged on the flexible tip portion 12. Each of the plurality of circumferential rings 40–48 preferably have the same outer diameter D as the outer diameter D' of the elongate tubular body member 10.

With respect to specific dimensional relationships it is clear that these could vary substantially. In addition the dimensions could and normally should vary between different catheter tip sizes. For example, there are currently standard catheter sizes referred to as "French" sizes e.g. size F4 is 0.053 inch diameter, F5 is 0.066 inch diameter, F6 is 0.079 inch diameter, F7 is 0.092 inch, and F8 is 0.104 inch. It is believed that the subject invention is applicable to all these sizes. To provide a full and complete enabling disclosure a preferred set of specific dimensions for the most commonly used F7 size is as hereafter set forth. Suitable dimensions for the remaining sizes can be readily determined by simple extrapolation and minor experimentation.

According to the preferred embodiment and with respect to a size F7 catheter, the outer diameter of the circumferential rings D as well as the outer diameter D' of the elongate tubular body member 10 is 0.092 in. Further, according to the preferred embodiment, each of the plurality of cut out regions 20–30 generate a reduced diameter d at spaced positions along the flexible tip portion 12. The diameter of regions 20–30 progressively decrease with region 20 being 5% less than D; region 22 being 10% less, region 24 being 15% less, region 26 being 17% less, region 28 being 20% less and region 30 being 25% less.

Further, in the preferred embodiment, each of the first through fifth cut out regions 20, 22, 24, 26, and 28 are of decreasing width along the longitudinal axis L of, respectively, 0.312 inches, 0.250 inches, 0.218 inches, 0.187 inches and 0156 inches. The sixth cut out region 30 extends from the fifth circumferential ring 48 to the opening 32 at the distal end B of the catheter device and is approximately 0.500 inches in length.

With continued reference to FIG. 1, pairs of the cut out regions 20–30 define the circumferential rings 40–48. The first circumferential ring 40 is the widest and has a width along the longitudinal axis L of the same width as the preceding cut out region 20. The second through fourth circumferential rings 42, 44 and 46, in turn, have widths which are equal to the width of the immediately preceding circumferential section. That is, circumferential ring 48. The second through fourth circumferential rings 42–46 have a width along the longitudinal axis L of 42 is 0.250 inches, 44 is 0.218 inches, 46 is 0.187 inches, while the width of the fifth circumferential ring 48 is 0.156 inches.

The preferred material is a flexible polyurethane which is available from G.F. Goodrich under the trade name Estane 58091/58092. This material is preferred because of its excellent torque response i.e. resistance to torsional twisting about the longitudinal axis L, and its ability to withstand high pressures such as when an opaque media is injected into an artery or other blood vessel. The tip material is Estane 58092 only. This gives the desired flexibility. The combination of this preferred polyurethane material with the preferred tip construction described above, provide excellent tip guide response.

Also with reference to FIG. 2, the lumen 50 of the elongate tubular body member 10 is illustrated as being co-extensive with approximately the same dimensions as the lumen 52 of the flexible tip portion 12. In the F7 size of the preferred embodiment, the diameter of the lumens of the elongate tubular body member 10 as well as the flexible tip portion 12 is between 0.046 and 0.056 inches.

Although the soft flexible catheter tip described above in connection with the preferred embodiment includes a plurality of circumferential rings defined by a corresponding plurality of cut out regions, alternative embodiments are also contemplated such as spiral cut out or built up regions or combinations of circumferential ring and/or spiral regions. Partially circumferentially extending regions are also possible alone or in combination with the above alternatives.

FIG. 3 shows a modified tip formed on the distal end of the FIGS. 1 and 2 catheter. Note that the distal end is defined by a frustoconical leading tip zone having a taper angle of approximately 5° and formed from a soft polyurethane material different than the polyurethane material forming the tubular body portion.

In addition, the present invention contemplates any and all patterns which may be formed on or in the flexible tip portion which define at least one region in the flexible tip portion of a transverse rigidity which is different than that defined by the elongate tubular member and the remainder of the catheter. The present invention accomplishes the varied transverse rigidity characteristics.

The invention has been described with reference to the preferred embodiment. Obviously, modifications and alterations will occur to others upon a reading and understanding of this specification. It is intended to include all such modification and alterations insofar as they come within the scope of the appended claims or the equivalents thereof.

Having thus described the invention, I now claim:

1. A catheter having a distal end adapted to be guided through blood vessels, comprising:

an elongated tubular member having i) a first innerbore therethrough along a longitudinal axis of the elongated tubular member and ii) a substantially uniform first transverse rigidity;

a flexible tip portion at a distal end of said elongated tubular member having a second innerbore therethrough along a second longitudinal axis of the flexible tip portion which is generally coextensive with said first longitudinal axis of the elongated tubular member; and, at least one region of a lesser second transverse rigidity on said flexible tip portion formed by a series of areas of decreasing transverse rigidity wherein said second transverse rigidity of said at least one region varies along said second longitudinal axis of said flexible tip portion and is provided by a portion of said flexible tip portion having an average transverse first cross sectional area along said second longitudinal axis less than a transverse second cross sectional area of the remainder of said flexible tip portion.

2. The catheter according to claim 1 wherein said at least one region of varying second transverse rigidity includes a plurality of regions each having a respective transverse rigidity less than said first transverse rigidity.

3. The catheter according to claim 2 wherein ones of said plurality of regions each having a respective transverse rigidity less than said first transverse rigidity are defined by respective portions of said flexible tip portion having an average transverse cross sectional area along said second longitudinal axis less than a transverse second cross sectional area of the remainder of said flexible tip portion.

4. The catheter according to claim 3 wherein all of said plurality of regions have an average transverse cross sectional area along said second longitudinal axis less than said transverse cross sectional area of the remainder of said flexible tip portion.

5. The catheter according to claim 4 wherein all of said plurality of regions have a single common respective transverse rigidity less than said first transverse rigidity.

6. The catheter according to claim 1 wherein said first innerbore of the elongated tubular member is of a first diameter and said second innerbore of the flexible tip portion is substantially of said first diameter.

7. The catheter according to claim 6 wherein the innerbore is of substantially constant cross-sectional area.

8. The catheter according to claim 1 wherein said elongated tubular member is formed of a polyurethane material and said flexible tip portion is formed from a soft polyurethane material different from the polyurethane material forming said elongated tubular member.

9. The catheter according to claim 8 wherein said elongated tubular member is a polyurethane material with a shore 60–63D.

10. A catheter apparatus comprising:
a tubular body portion formed from a polyurethane material and defining a longitudinal axis of the catheter apparatus; and,
a tubular tip portion formed from a soft polyurethane material, the tubular tip portion defining a plurality of axially spaced apart circumferential rings and further wherein a first one of the plurality of axially spaced apart circumferential rings has a first width along the longitudinal axis of the catheter apparatus and a second one of the plurality of axially spaced apart circumferential rings has a second width along the longitudinal axis different from the first width.

11. The catheter apparatus according to claim 10 wherein said tubular tip portion includes a pliable frustoconical leading tip zone defining the distal end of the catheter apparatus.

12. The catheter apparatus according to claim 11 wherein said frustoconical leading tip zone is formed from a soft polyurethane material different from the polyurethane material forming said tubular body portion.

13. The catheter apparatus according to claim 12 wherein said frustoconical leading tip zone has a taper angle of approximately 5°.

14. The catheter apparatus according to claim 10 wherein said frustoconical leading tip zone has a transverse cross-sectional outer diameter which decreases to a smaller transverse cross-sectional outer diameter at the distal end of the catheter apparatus.

15. A catheter apparatus comprising:
a tubular body portion formed from a polyurethane material and defining a longitudinal axis of the catheter apparatus; and,
a tubular tip portion formed from a soft polyurethane material the tubular tip portion defining a plurality of axially spaced apart circumferential rings and further wherein the soft polyurethane material is Estane 5094.

16. The catheter apparatus according to claim 10 wherein:
said first one of the plurality of axially spaced apart circumferential rings is disposed on the catheter apparatus between said second one of the plurality of axially spaced apart circumferential rings and the distal end of the catheter apparatus; and,
said first width is less than said second width.

17. The catheter apparatus according to claim 10 wherein:
a first one of the plurality of axially spaced apart circumferential rings has a first width along the longitudinal axis of the catheter apparatus;
a second one of the plurality of axially spaced apart circumferential rings has a second width along the longitudinal different from the first width; and,
a first set of at least three of the plurality of axially spaced apart circumferential rings have a third width along the longitudinal different from the first and second widths.

18. The catheter apparatus according to claim 17 wherein:
said first one of the plurality of axially spaced apart circumferential rings is disposed on the catheter apparatus between said second one of the plurality of axially spaced apart circumferential rings and the distal end of the catheter apparatus;
said first set of at least three of the plurality of axially spaced apart circumferential rings is disposed on the catheter apparatus between said second one of the plurality of axially spaced apart circumferential rings and said first one of the plurality of axially spaced apart circumferential rings;
said first width is less than said third width; and,
said third width is less than said second width.

\* \* \* \* \*